US008095544B2

(12) United States Patent
Boone et al.

(10) Patent No.: US 8,095,544 B2
(45) Date of Patent: Jan. 10, 2012

(54) METHOD, SYSTEM, AND APPARATUS FOR VALIDATION

(75) Inventors: Keith W. Boone, Randolph, MA (US); Sunitha Chaparala, Weymouth, MA (US); Sean Gervais, Dorchester, MA (US); Robert G. Titemore, Lexington, MA (US); Harry J. Ogrinc, Westwood, MA (US); Jeffrey G. Hopkins, Lincoln, RI (US); Roubik Manoukian, Belmont, MA (US); Cameron Fordyce, Providence, RI (US)

(73) Assignee: Dictaphone Corporation, Stratford, CT (US)

(*) Notice: Subject to any disclaimer, the term of this patent is extended or adjusted under 35 U.S.C. 154(b) by 425 days.

(21) Appl. No.: 10/448,317

(22) Filed: May 30, 2003

(65) Prior Publication Data

US 2004/0243614 A1    Dec. 2, 2004

(51) Int. Cl.
G06F 7/00 (2006.01)
G06F 17/30 (2006.01)
(52) U.S. Cl. ........ 707/750; 707/728; 707/727; 707/723; 707/730
(58) Field of Classification Search .................. 705/2, 3; 707/102, 750, 730; 715/513; 1/1
See application file for complete search history.

(56) References Cited

U.S. PATENT DOCUMENTS

| | | | |
|---|---|---|---|
| 4,477,698 A | 10/1984 | Szlam et al. | |
| 4,965,763 A | 10/1990 | Zamora | |
| 5,253,164 A | 10/1993 | Holloway et al. | |
| 5,325,293 A | 6/1994 | Dorne | |
| 5,327,341 A | 7/1994 | Whalen et al. | |
| 5,392,209 A | 2/1995 | Eason et al. | |
| 5,664,109 A | 9/1997 | Johnson et al. | |
| 5,799,268 A | 8/1998 | Boguraev | |
| 5,809,476 A | 9/1998 | Ryan | |
| 5,832,450 A * | 11/1998 | Myers et al. | ....... 705/3 |
| 5,970,463 A | 10/1999 | Cave et al. | |
| 5,974,412 A | 10/1999 | Hazlehurst et al. | |
| 6,006,221 A | 12/1999 | Liddy et al. | |
| 6,014,663 A | 1/2000 | Rivette et al. | |
| 6,021,202 A | 2/2000 | Anderson et al. | |
| 6,052,693 A | 4/2000 | Smith et al. | |
| 6,055,494 A | 4/2000 | Friedman | |
| 6,088,437 A | 7/2000 | Amick | |
| 6,182,029 B1 | 1/2001 | Friedman | |
| 6,192,112 B1 | 2/2001 | Rapaport et al. | |
| 6,289,353 B1 | 9/2001 | Hazlehurst et al. | |
| 6,292,771 B1 | 9/2001 | Haug et al. | |
| 6,347,329 B1 | 2/2002 | Evans | |

(Continued)

OTHER PUBLICATIONS

Smith, et al., "Microarras: An Advanced Full-Text Retrieval and Analysis System", ACM 1987, p. 187-195.

(Continued)

*Primary Examiner* — Tony Mahmoudi
*Assistant Examiner* — Paul Kim
(74) *Attorney, Agent, or Firm* — Wolf, Greenfield & Sacks, P.C.

(57) ABSTRACT

In a method for validating data, a text of a document is received. At least one fact is extracted from the text. At least one expert refinement is merged with the at least one fact to create at least one modified fact. The at least one modified fact is provided for a review. An expert refinement to the at least one modified fact is captured in response to the review. A superset document based on the at least one pre-existing refinement and the expert refinement is stored.

31 Claims, 9 Drawing Sheets

U.S. PATENT DOCUMENTS

| | | | |
|---|---|---|---|
| 6,360,215 | B1 | 3/2002 | Judd et al. |
| 6,405,165 | B1 | 6/2002 | Blum et al. |
| 6,434,547 | B1 | 8/2002 | Mishelevich et al. |
| 6,438,533 | B1 | 8/2002 | Spackman et al. |
| 7,233,938 | B2 | 6/2007 | Carus et al. |
| 2002/0007285 | A1* | 1/2002 | Rappaport ............... 705/2 |
| 2002/0095313 | A1* | 7/2002 | Haq ............... 705/2 |
| 2002/0128861 | A1* | 9/2002 | Lau et al. ............... 705/2 |
| 2003/0208382 | A1* | 11/2003 | Westfall ............... 705/3 |
| 2004/0186746 | A1* | 9/2004 | Angst et al. ............... 705/3 |
| 2004/0220895 | A1 | 11/2004 | Carus et al. |
| 2004/0243545 | A1 | 12/2004 | Boone et al. |
| 2004/0243551 | A1 | 12/2004 | Boone et al. |
| 2004/0243552 | A1 | 12/2004 | Titemore et al. |
| 2005/0108010 | A1 | 5/2005 | Frankel et al. |
| 2005/0114122 | A1 | 5/2005 | Uhrbach et al. |
| 2005/0120020 | A1 | 6/2005 | Carus et al. |
| 2005/0120300 | A1 | 6/2005 | Schwager et al. |
| 2005/0144184 | A1 | 6/2005 | Carus et al. |

OTHER PUBLICATIONS

U.S. Appl. No. 11/068,493, Carus, et al.
U.S. Appl. No. 10/953,471, Cote, et al.
U.S. Appl. No. 11/069,203, Cote, et al.
U.S. Appl. No. 11/007,626, Cote, et al.
U.S. Appl. No. 10/840,428, Carus, et al.
U.S. Appl. No. 10/951,281, Cote, et al.
"Hardware Reference Manual," Release 3 for DOS, revised Jan. 1994, PIKA Technologies, Inc., Ontario, Canada, available at http://www.pikatechnologies.com/downloads/legacy/AVA%20B-Series%20Hardware%20Manual.pdf (last accessed Jul. 25, 2005).
"Customizing D/41 Call Analysis," date unknown, Intel Corp., Santa Clara, California, available at http://resource.intel.com/telecom/support/appnotes/custd41d.htm (last accessed Jul. 25, 2005).
Fei Song et al., A Graphical Interface to a Semantic Medical Information System, *Journal of Foundations of Computing and Decision Sciences*, 22(2), 1997.
Fei Song et al., A Cognitive Model for the Implementation of Medical Problem Lists, *Proceedings of the First Congress on Computational Medicine, Public Health and Biotechnology*, Austin, Texas, 1994.
Fei Song et al., A Graphical Interface to a Semantic Medical Information System, *Karp-95 Proceedings of the Second International Symposium on Knowledge Acquisition, Representation and Processing*, pp. 107-109, 1995.
*Epic Web Training Manual*, pp. 1-33, 2002.
B. Hieb, Research Note, NLP Basics for Healthcare, Aug. 16, 2002.
C. Shalizi et al., Pattern Discovery in Time Series, Part I: Theory, Algorithm, Analysis, and Convergence, Journal of Machine Leaning Research (2002) Submitted Oct. 28, 2002; Published 2002.
C. Nevill-Manning et al., The Development of Holte's 1R Classifier, Department of Computer Science.
D. Cutting et al., A Practical Part-of-Speech Tagger, Xerox Palo Alto Research Center.
J. Zavrel et al., Recent Advances in Memory-Based Part of Speech Tagging, ILK/Computational Linguistics.
E. Brill, Some Advances in Transformation-Based Part of Speech Tagging, Spoken Language Systems Group.
J. Nivre, DAC723: Language Technology Finite State Morphology, Vaxjo University of Mathematics and Systems Engineering, pp. 1-11.
M. Creutz, Morphology and Finite-State Transducers, Oct. 31, 2001, Chap 3, Jurafsky & Martin.
http://www.comp.lancs.ac.uk/computing/research/stemming/general/index.htm printed Jul. 19, 2004.
http://www.comp.lancs.ac.uk/computing/research/stemming/general/stemmingerrors.htm printed Jul. 19, 2004.
http://www.comp.lancs.ac.uk/computing/research/stemming/general/performance.htm; printed Jul. 19, 2004.
M. Lee et al., Cleansing Data for Mining and Warehousing, Lecture Notes in Computer Science, vol. 1677 archive, Proceedings of the 10$^{th}$ International Conference on Database and Expert Systems Applications, pp. 751-760, Springer-Verlag, London, 1999.
C. Van Rijsbergen, Information Retrieval, 2$^{nd}$ Ed., Ch. 5, Butterworths, London, 1979.
J. Day, Extracting Knowledge from Text Using Learning by Constraint Relaxation (LCR), CSI, www.csi-inc.com/CSI/pdf/jday_icim02.pdf.
W. Gale et al., Discrimination Decisions for 100,000-Dimensional Spaces, Current Issues in Computational Linguistics, pp. 429-450, Kluwer Academic Publishers, 1994.
W. Daelemans et al., TiMBL: Tilburg Memory Based Learner, version 5.0, Reference Guide, ILK Research Group Technical report Series No. 04-02 (ILK-0402), ILK Research Group, Tilburg University, Tilburg, Netherlands, 2004.
Case Study: Massachusetts Medical Society http ://www.microsoft.com/resources/casestudies/CaseStudy.asp?CaseStudyID=14931, posted Jan. 13, 2004.
W. Braithwaite, Continuity of Care Record (CCR) http://www.h17.org/library/himss/2004Orlando/ContinuityofCareRecord.pdf.
C. Waegemann, EHR vs. CCR: What is the difference between the electronic health record and the continuity of care record?, Medical Records Institute, 2004.
Press Release: Kryptiq Announces Support of CCR Initiative and Introduces New Solutions that Enable Information Portability, Accessibility and Clinical System Interoperability http://www.kryptiq.com/News/PressReleases/27.html, posted Feb. 17, 2004.
Work Item Summary: WK4363Standard Specification for the Continuity of Care Record (CCR), http://www.astm.org/cgi-bin/SoftCart.exe/Database.Cart/Workitems/WK4363.htm?E+mystore, Mar. 3, 2004.
Continuity of Care Record (CCR): The Concept Paper of the CCR, v. 2.1b, http://www.bhtinfo.com/CCR.Concept%20Paper.1.5.doc.
Continuity of Care Record, American Academy of Family Physicians, http:///www.aafp.org/x24962.xml?printxml, posted Nov. 12, 2003.
Continuity of Care Record (CCR). AAFP Center for Health Information Technology, http:///www.centerforhit.org/x201.xml , posted Aug. 20, 2004.
Core Measures web page, Joint Commission on Accreditation of Healthcare Organizations, http://www.jcaho.org/pms/core+measures/, printed Mar. 22, 2004.
Specifications Manual for National Implementation of Hospital Core Measures, v.2.0, Joint Commission on Accreditation of Healthcare Organizations, http://www.jcaho.org/pms/core+measures/information+on+final+specifications.htm.
Code information and Education web page, American Medical Association, http://www.ama-assn.org/ama/pub/category/3884.html, printed Mar. 22, 2004.
Category III CPT Codes, American Medical Association, http://www.ama-assn.org/ama/pub/article/3885-4897.html, printed Mar. 22, 2004.
ICD-9-CM Preface (FY04), http://ftp.cdc.gov/pub/Health_Statistics/NCHS/Publications/ICD9-CM/2004/Prefac05.RTF.
ICD-9-CM Official Guidelines For Coding and Reporting, effective Oct. 1, 2003.
Q.X. Yang et al., "Faster algorithm of string comparison", Pattern Analysis and Applications, vol. 6, No. 1, pp. 122-133, Apr. 2003.

\* cited by examiner

Validation - Microsoft Internet Explorer

Facts and Mentions | Finish | Save | Exit

Importance: 🔔 = Important in Current Report | Current List: ☐ = Current ◆ = Not current (Click to change)

Problems (9 found) | Medications (7 found) | Allergies (2 found)
- 🔔 ☐ Chronic tophaceous gout
- 🔔 ☐ Derangement of knee
- 🔔 ☐ Finding of body region
- 🔔 ☐ Gout NOS
- 🔔 ☐ Polyserositis
- ✓ ◆ Spinal stenosis
- ✗ ◆ Unknown
- ✓ ◆ (Gout NOS)
- ✓ ◆ (Neonatal renal disorder)

Medications:
- 🔔 ◆ Amlodipine
- ✓ ☐ Colchicine
- ✓ ◆ Lasix
- ✓ ☐ Lisinopril
- ✓ ◆ Ranitidine
- ✓ ☐ Penicillin
- ✓ ◆ Sulfa Allergies:
- 🔔 ☐ Allopurinol
- 🔔 ☐ Probenecid

Procedures (3 found)

History
- ✓ Cholecystectomy
- ✓ Lobectomy
- ✓ Removing The Tophi

Validation: ✓ = Correct ✗ = Incorrect

✓ 2 Mentions of Colchicine
- ✓ ... any chronic management other than taking some colchicine.
- ✓ ... Lasix, _____, lisinopril, colchicine, ranitidine.

✗ Click to set all incorrect.

Current Report | Previous Mention | Next Mention other than taking some ✓colchicine. He told me that at one point, he tried ✓allopurinol and at another point, he tried ✓probenecid but did not take either for very long because he has gastric intolerance to those two. He is not aware of any ✓renal dysfunction but also reports that he really has not had any comprehensive evaluation of management of his ✓gout. It effects his hands at least his toe on one side.
REVIEW OF SYSTEMS: Positive for ✓cholecystectomy, prior ✓lobectomy, ✓spinal stenosis.
MEDICATIONS: ✓Amlodipine ✓Lasix, _____, ✓lisinopril ✓colchicine ✓ranitidine.
ALLERGIES: ✓PENICILLIN AND ✓SULFA.
PERSONAL HISTORY: No smoking. Drinks alcohol, ?one per day.
PHYSICAL EXAMINATION: On examination today. I found that the patient's ✗gouty deposits are obviously present in the affected fingers in a

FIG. 4

Validation - Microsoft Internet Explorer

Facts and Mentions

Importance: 🏛 = Important in Current Report — 510     Current List: ☐ = Current ◆ = Not current (Click to change) — 512

Problems (9 found)                    Medications (7 found)         Allergies (2 found) — 514
☐ Chronic tophaceous gout                 ◆ Amlodipine                      ☐ Allopurinol
☐ Derangement of knee                     ☐ Colchicine                      ☐ Probenecid
☐ Finding of body region                  ◆ Lasix
☐ Gout NOS                                ☐ Lisinopril                                                    516
☐ Polyserositis                           ◆ Ranitidine
☐ Spinal stenosis                         ☐ Penicillin                      Procedures (3 found)
✗ Unknown                                 ◆ Sulfa                           History
◆ *(Gout NOS)*                                                                  Cholecystectomy
◆ *(Neonatal renal disorder)*                                                   Lobectomy
                                                                                Removing The Tophi
524                                                                       518

(Finish) (Save) (Exit)
  504    506   508

Validation - Microsoft Internet Explorer

Facts and Mentions

History
◆ Aortic valve disorder | Change Fact
◆ Coronary atherosc | Change Negation
◆ Disease of intestin | Make History
✗ Unknown             | Make Current
                      | Make Family History
                      | Make Social History
524                   | Make Mention (Finish) (Save) (Exit)

Validation-Microsoft Internet Explorer

Facts and Mentions | Finish | Save | Exit

Validation: ✓ = Correct ✗ = Incorrect

✓ 2 Mentions of Colchicine
✗ ... any chronic management other than taking some colchicine.
✗ ... Lasix, _____, lisinopril, colchicine, ranitidine.

✗ Click to set all incorrect.

Previous Mention | Next Mention

Current Report other than taking some ✓colchicine. He told me that at one point, he tried ✓allopurinol and at another point, he tried ✓probenecid but did not take either for very long because he has gastric intolerance to those two. He is not aware of any ✓renal dysfunction but also reports that he really has not had any comprehensive evaluation of management of his ✓gout. It effects his hands at least his toe on one side.
REVIEW OF SYSTEMS: Positive for ✓cholecystectomy, prior ✓lobectomy, ✓spinal stenosis.
MEDICATIONS: ✓Amlodipine ✓Lasix, _____, ✓lisinopril ✓colchicine ✓ranitidine.
ALLERGIES: ✓PENICILLIN AND SULFA.
PERSONAL HISTORY: No smoking. Drinks alcohol, ?one per day.
PHYSICAL EXAMINATION: On examination today. I found that the patient's Xgouty deposits are obviously present in the affected fingers in a 430, 420, 602, 604

FIG. 7

Validation-Microsoft Internet Explorer

Facts and Mentions | Finish | Save | Exit

✓ 2 Mentions of Colchicine
✗ ... any chronic management other than taking some colchicine. ← 702
✗ ... Lasix, _____, lisinopril, colchicine, ranitidine.

✗ Click to set all incorrect.

430, 704

METHOD, SYSTEM, AND APPARATUS FOR VALIDATION

CROSS-REFERENCE TO RELATED APPLICATIONS

This application relates to co-pending U.S. patent application Ser. No. 10/447,290, entitled "SYSTEMS AND METHODS UTILIZING NATURAL LANGUAGE MEDICAL RECORDS," filed on May 29, 2003; co-pending U.S. patent application Ser. No. 10/413,405, entitled "SYSTEMS AND METHODS FOR CODING INFORMATION," filed Apr. 15, 2003; co-pending U.S. patent application Ser. No. 10/448,320, entitled "METHOD, SYSTEM, AND APPARATUS FOR DATA REUSE," filed on May 30, 2003; and co-pending U.S. patent application Ser. No. 10/448,325, entitled "METHOD, SYSTEM, AND APPARATUS FOR VIEWING DATA," filed on May 30, 2003; all of which are hereby incorporated by reference in their entirety.

BACKGROUND OF THE INVENTION

The present invention relates generally to validating data from text extracted from a set of records. More specifically, the present invention relates to capturing and applying refinements made by a domain expert to the validity, relevance, and temporal significance of "facts" (extractions of discreet data elements, their location within the document, their normalizations, and their ontological classifications) automatically extracted from electronic text.

In the medical field, health care providers (e.g., physicians, medical technicians or administrators) typically dictate diagnoses, medications and other patient medical reports in a free form manner. These dictations are then transcribed into documents. The transcribed documents are typically then submitted to the provider for review and approval. The transcribed documents will likely contain data that is relevant to different users at different times. Additionally, many legacy databases contain documents that include data with varying degrees of relevancy.

Automatic extraction of specified data from electronic medical records has been known for some time. It is well known in the art that computation algorithms may be employed to process text of an electronic document to extract specific data from the document. However, validating the relevancy, relevance, classification, and temporal significance of the data has not been possible heretofore.

Presently, users are required to manually review extracted data in order to validate the data. The manual process requires review of the text document, a time consuming review process in which the user may edit and approve the text for ultimate storage in a database where the text may be reviewed at a later time. Manual operation may include data entry using drop down menus, mouse pointing clicks, typing and time consuming records review. It is therefore desirable to provide users with a validation process that utilizes automatically extracted, relevant data items from free form dictated and transcribed documents.

The significance of facts can change over time. A deficiency in current systems that perform extraction is that they do not account for the temporal significance of the fact. For example, a problem that is relevant today may be resolved tomorrow, and thus the fact that the problem exists is true only when the context of the time period (today) is provided.

An additional problem exists relating to nomenclature. There are several ways to describe many different physical ailments. More particularly, users of such systems often use different phrases to describe a single type of event. For example, one physician may use 'myocardial infarction' while another physician may use 'heart attack' to describe a problem for a patient. In this example, there may be up to 25 phrases that describe the same or similar ailment to the heart. As such, a searcher who wishes to find a group of records that involve a particular term of art would have to know and use of all the variants of those phrases in order to ensure a complete search. It would be desirable to provide a grouping of like and similar variants of key medical facts, medical concepts, and present those in a user interface along with extractions of the discrete data elements.

Health care providers are often responsible for maintaining lists of current problems, medications, allergies, and procedures for patients. Problems in this context can be anything that is relevant to the physician or affects the care and treatment of the patient. Facts on the current list are significant over a particular time period, after which the problem may no longer be relevant to the patient's treatment and care, or the patient's problem may have been resolved, or the medication discontinued, et cetera.

Manual processes for maintaining these lists often include paper forms wherein the provider writes in new items on the list, dates it, and signs it, or through dictation wherein the provider dictates the actual insertions and removals, where these changes are then made by clerical personnel at the time the dictated report is transcribed. Automated processes found in electronic medical record systems require data entry of the items on the current list.

The deficiencies inherent in manual processes are numerous. When a paper form is used, only one copy of it is available, whereas when this information is stored electronically, multiple viewers can access the information at the same time. It is difficult to locate information on paper forms or even in electronic documents as these storage mechanisms do not provide sorting and filtering features that might be available when the information is stored in a database. A further problem is that when the provider dictates changes to the list, there are time lags introduced by the transcription and editing process that create a delay between the dictation of these changes and the actual implementation of these changes on the storage media. This imposes a delay on the availability of changes to the provider and to the rest of the medical community providing patient care.

When current lists are maintained in electronic medical record systems, the user must manually enter the information in the list, rather than have the system suggest to them changes that might be made to the current list based on extracted facts.

Finally, when current lists are maintained on forms, through dictated changes, or even in electronic medical records, the context in which the problem, medication, allergy, or procedure mentioned for the patient is not available. Therefore, the only information available to the medical community is the item on the current list, without more detailed context that might provide for better medical care.

Thus, present systems do not have the ability to integrate information in real time to a current lists report and cannot provide context for that information. It is desirable to provide a system that presents discrete data elements for approval in real time by a user with the ability to determine the context of a report, namely, the creation point of the report, the creator, the time frame and the relevance of the discrete element for extraction.

OBJECTS OF THE INVENTION

In light of the above-identified prior art deficiencies, it is an object of the present invention to provide a system and method to validate a freeform text document for certain facts as true or relevant to a case before they are stored in a database and marked as such.

It is another object of the present invention to provide a system and method by which a user may approve or validate extracted data prior to sending it to the database for a subsequent retrieval and viewing inquiry.

It is still another object of the present invention to provide a system and method for validating extracted data applicable to third party systems, such as a hospital information system or an EMR.

It is another object of the present invention to provide a system and method for validating extracted data and maintaining a current list.

It is another object of the present invention to provide a system and method for validating extracted data and maintaining a current list indexed and searchable by multiple degrees, namely, to determine the status of a record as of a specified date.

It is another object of the present invention to provide a system and method for validating extracted data where a user may review specific extracted data elements to further refine the extracted information.

It is another object of the present invention to provide a system and method for validating extracted data and maintaining a current list by carrying forward the information pre-determined as relevant or true until a user specified change.

It is another object of the present invention to capture information about the time that a fact was observed or reported upon, and/or the time that a counter-example to the fact was observed or reported upon, in order to maintain information about the temporal significance of said fact.

SUMMARY OF THE INVENTION

An advantage exists in the present invention, which facilitates the determination of validity, relevance, classification, and temporal significance of facts, automatically extracted from electronic text for capturing and applying refinements made by a domain expert.

In a first aspect, the present invention includes a method of reviewing data. The method includes receiving the text of a document and at least one fact, capturing an expert refinement to the at least one fact in response to the review, and storing a superset document based on the at least one pre-existing fact and the expert refinement. The method may also include the at least one fact from the text being subsequently merged with a previously stored expert refinement to produce at least one modified fact and the capturing of expert refinements is applied to modified facts. The receiving of the text of the document may also include receiving the document by one of electronic mail, file transport protocol, and a network file transfer protocol. The providing of the review document for the review may also include providing a graphical user interface adapted to display the at least one modified fact and highlighting a selected fact displayed on the graphical user interface. The method may also include displaying at least one category of facts, the selected fact being a member of the at least one category of facts, displaying a related details category for the selected fact, and displaying the selected text and surrounding text (i.e., the context) of the selected fact in the graphical user interface. The method may also include displaying a relevancy indicator for each fact in the at least one category of facts. The method may also include displaying a truthfulness indicator for each fact in the at least one category of facts. The method may also include providing the at least one modified fact and the text to a domain expert and determining the expert refinement based on a review of the at least one modified fact and the at least one expert refinement by the domain expert. The method may also include storing the expert refinement as an expert refinement file, collecting a set of related documents based on an index, extracting the at least one fact based on the set of related documents, and providing the at least one fact to a domain expert. The related documents may be of similar date, topic or clustered by similar content using any number of document clustering and classification algorithms well known to those practiced in the art (e.g., K-nearest neighbor algorithm, or cosine similarity metric). The method may also include determining a set of normalized facts based on the at least one fact, for example, by classifying facts to a taxonomy such as SNOMED or to the ICD-9-CM, or CPT, or other such taxonomy, not necessarily limited to the medical domain. The method may also include providing the set of normalized facts with the at least one modified fact for the review, and determining a temporal significance for the at least one modified fact, for example by recording the date the fact was observed based on metadata included with the medical record. The method may also include determining a relevancy factor for the at least one modified fact and providing the relevancy factor with the at least one modified fact for the review.

In a second aspect, the present invention includes a system for validation. The system includes an extraction module configured to extract a set of facts from a captured electronic document, a storage device configured to interface with the extraction module and the validation module, and a validation module configured to provide a graphical user interface to validate the facts, wherein the validation module is configured to receive a set of facts from the extraction module, apply a set of expert facts retrieved from storage device to the set of facts to create a set of modified facts, and provide the set of modified facts to an author for review. The validation module may be further configured to determine a set of normalized facts for the set of facts. The validation module may be further configured to determine a temporal significance for the set of facts. The validation module may be further configured to determine a relevancy factor for the set of facts. The validation module may be further configured to provide at least one of a set of normalized facts, a temporal significance, and a relevancy factor with the set of facts to a domain expert. The validation module may be further configured to capture modifications to the set of facts as the set of expert facts based on a review of the at least one of the set of normalized facts, the temporal significance, and relevancy factor with the set of facts by the domain expert. The validation module may be further configured to store the set of expert facts.

The above advantages and features are of representative embodiments only, and are presented only to assist in understanding the invention. It should be understood that they are not to be considered limitations on the invention as defined by the claims, or limitations on equivalents to the claims. Additional features and advantages of the invention will become apparent from the drawings, the following description, and the claims.

BRIEF DESCRIPTION OF THE DRAWINGS

While the specification concludes with claims particularly pointing out and distinctly claiming the present invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the figures, wherein:

FIG. 4 illustrates a validation viewer GUI provided by the validation client module in accordance with yet another embodiment of the present invention;

FIG. 5 illustrates the target viewer component in greater detail in accordance with yet another embodiment of the present invention;

FIG. 5A illustrates an expanded view of a current list included in the target viewer component in accordance with another embodiment of the present invention;

FIG. 6 illustrates a more detailed view of the record viewer component in accordance with yet another embodiment of the present invention;

FIG. 7 illustrates a more detailed view of the extractions viewer component in accordance with yet another embodiment of the present invention;

DETAILED DESCRIPTION OF THE EMBODIMENTS

Figure 1:
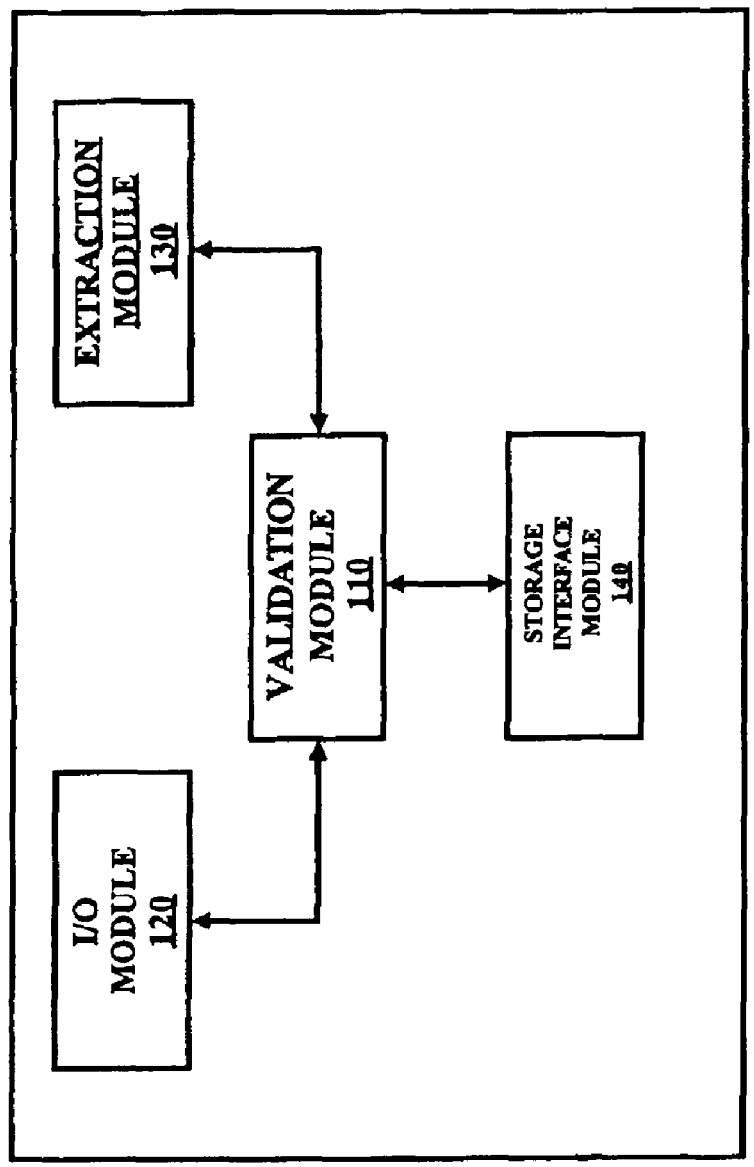
FIG. 1 illustrates an exemplary architecture of a validation client module in accordance with an embodiment of the present invention.

For simplicity and illustrative purposes, the principles of the present invention are described by referring mainly to exemplary embodiments thereof. However, one of ordinary skill in the art would readily recognize that the same principles are equally applicable to, and can be implemented in, all types of network systems, and that any such variations do not depart from the true spirit and scope of the present invention. Moreover, in the following detailed description, references are made to the accompanying figures, which illustrate specific embodiments. Electrical, mechanical, logical and structural changes may be made to the embodiments without departing from the spirit and scope of the present invention. The following detailed description is, therefore, not to be taken in a limiting sense and the scope of the present invention is defined by the appended claims and their equivalents.

Embodiments relate to validating data extracted from a document. In one embodiment, a host application instantiates a validation client module and forwards a document to the validation client module. The validation client module is configured to capture a document. The document may be in an electronic format such as commercial word processing file, ASCII, mark-up language, or other similar format. The validation client module is also configured to extract a set of discrete data elements (e.g., facts, keywords, or other similar data) from the captured electronic text. It will be understood by those skilled in the art that the present invention can be applied to freeform dictated documents as well as to any electronic text, free narrative or otherwise.

More particularly, the validation module may use parsing engines to parse for relevant facts within the captured electronic text. The validation client module may be further configured to merge a previously determined set of validated facts to the extracted set of facts as a preliminary set of facts. The validation client module may be further configured to normalize the extracted facts, determine the temporal significance for the preliminary set of facts, and/or to determine the relevance of the modified set of facts as preliminary metadata. The validation client module may record the time that a fact or its counter-example was observed or reported upon in order to determine the temporal significance of said fact.

The validation client module may be further configured to provide the preliminary metadata, the preliminary set of facts, and the text of the document to a domain expert for review. The validation client module may then receive expert refinements, i.e., changes, based on a review of the preliminary metadata, the preliminary set of facts, and the text of the document. The validation client module may then be configured to store the changes to the preliminary metadata and set of facts as expert refinements. The expert refinements are associated with the document and returned to the host application. In one embodiment, the validation client module may be configured to maintain a delta file that captures the changes that occurred during the review of the preliminary metadata and the preliminary set of facts. The validation client module may be further configured to maintain and permanently store the delta files for each document. In another embodiment, the validation client module may be configured to provide preliminary metadata and the preliminary set of facts on a set of related documents. The set of related documents may be related chronologically, subject, or other similar indexing key. The validation client module then accepts expert refinements based on the review of the domain expert for the set of related documents.

Accordingly, the validation client module may provide a mechanism for a user to quickly evaluate and validate facts from a document. By associating the validated facts with a document, the search capability for the document may be increased. More specifically, the validated facts may become search terms for the document and thus increase the precision of the search.

FIG. 1 illustrates an exemplary architecture of a validation client module 100 in accordance with an embodiment. It should be readily apparent to those of ordinary skill in the art that the exemplary architecture depicted in FIG. 1 represents a generalized schematic illustration and that other elements may be added or existing elements may be removed or modified.

As shown in FIG. 1, the validation client module 100 includes a validation module 110, an input/output (I/O) module 120 (labeled as 'I/O module' in FIG. 1), an extraction module 130, and a storage interface module 140. The validation module 110 may be configured to provide the functionality for the validation client module 100. For example, the validation module 110 may invoke the I/O module 120 to provide for a validation graphical user interface (GUI) in response to initiating the validation client module 100. As another example, the validation module 110 may invoke the extraction module 130 to extract at least one fact from a selected document. As yet another example, the validation module 110 may merge extracted facts with a set of facts extracted from a previous version and/or group of documents. The validation module 110 may also determine similar terms for a selected fact, i.e., normalize the selected fact.

The I/O module 120 may be configured to provide a mechanism for a user to communicate with the validation client module 100. For example, the I/O module 120 may be invoked to provide a GUI for a domain expert to review extracted facts. The I/O module 120 may also provide another GUI to receive revisions to extracted facts.

The extraction module 130 may be configured to extract facts from a selected document when invoked by the validation module 110. The extraction module 130 may be implemented by conventional extraction software (e.g., those implemented by applying a collection of regular expressions to a document). The extraction module 130 may return the extracted facts to the validation module 110.

The storage interface module 140 may be configured to provide access to storage devices by the validation module 110. The storage interface module 140 may retrieve and store previous validated facts for a document (or group of documents), normalization data for facts, categorization data for facts, versions of the validated facts for a selected document, etc., for the validation module 110. The storage interface module 140 may be implemented as a physical drive interface (e.g., IDE, SCSI, IEEE1394, etc.), a device driver library or other similar interfacing technique.

Accordingly, the validation client module 100 may be adapted to be invoked by a host application. The validation client module 100 may be configured to receive a document or a pointer to the document from the host application. The validation module 110 may be configured to invoke the extraction module 130 to extract facts from the document. The extraction module 130 may be configured to return the extracted facts, to the validation module 110.

The validation module 110 may be configured to retrieve previous expert refinements, if any, through the storage interface module 140. The validation module 110 combines the current facts with any previous expert refinements to create a preliminary set of facts. The validation module 110 may then invoke the I/O module to provide for a graphical user interface (GUI) that displays the preliminary set of facts, the text of the current document and the preliminary metadata. The validation module 110 may be further configured to capture any changes implemented by a domain expert, i.e., a user with proper authority, on the GUI, as an expert refinement file. The validation module 110 may be further configured to maintain a delta file of the changes made by the domain expert.

The validation module 110 is configured to associate the expert refinement file with the document and return the files (by copy or link) to the host application. The validation module 110 may be further configured to store the expert refinement file and delta file by passing the files to the storage interface module 140. Accordingly, the validation module 110 may retrieve the expert refinement file to perform validation on new versions of the document.

It should be readily apparent to those skilled in the art that the individual functions, as described above and in further details below, embodied by the respective I/O module 120, extraction module 130, and storage interface module 140 may be performed by the validation module 110. Conversely, the individual functions, as described above and in further details below, of the validation module 110 may be moved to the I/O module 120, extraction module 130, and storage interface module 140.

The validation client module 100 may be implemented as a software program, a utility, a subroutine, or other similar programming entity. In this respect, the validation client module 100 may be implemented using software languages such as C, C++, JAVA, etc. Alternatively, the validation client module 100 may be implemented as an electronic device utilizing an application-specific integrated circuit, discrete components, solid-state components or a combination thereof.

Figure 2:
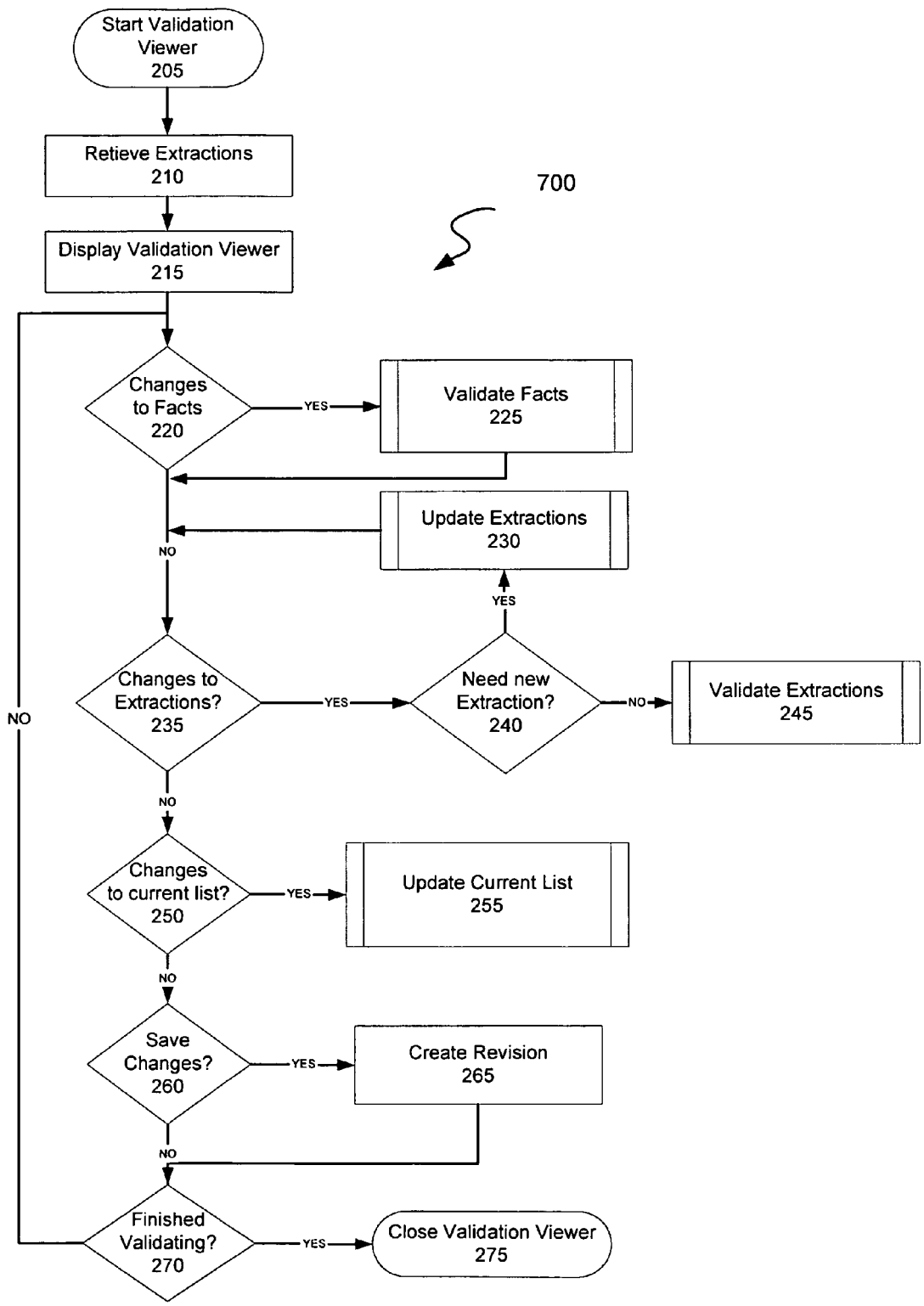
FIG. 2 illustrates an exemplary flow diagram for the validation client module in accordance with another embodiment of the present invention.

FIG. 2 illustrates an exemplary flow diagram 200 for the validation client module 100 in accordance with another embodiment. It should be readily apparent to those of ordinary skill in the art that this method 200 represents a generalized illustration and that other steps may be added or existing steps may be removed or modified.

As shown in FIG. 2, the validation client module 100 may be invoked by a host application (not shown), in step 205. For example, the host application may receive activation of a menu item that represents the validation client module 100, perform a function call to the validation client module 100, or a user may execute a command line to instantiate the validation client module 100. Alternatively, the validation client module 100 may be a standalone application program.

In step 210, the validation module 110 may invoke the extraction module 130 to extract facts from a selected document. The document or a pointer to the document may have passed to the validation module 110 when the validation client 100 was invoked. The extraction module 130 may utilize a conventional extraction module to extract the facts (or keywords, concepts, etc.) from the selected document. The extraction module 130 may be configured to return the extracted facts to the validation module 110.

In step 215, the validation module 110 may invoke the I/O module 120 to provide a validation viewer GUI (not shown). The validation viewer may provide a mechanism to review the extracted facts along with access to previous validated facts. The validation viewer GUI may comprise a target viewer component, a record viewer component, and an extraction viewer component. The target viewer component may present the extracted facts into target groups (e.g., Problems, Medications, Allergies). The extraction viewer GUI presents an extracted fact in the context of a single line of the report. This enables an authorized user to quickly determine whether or not the selected fact is valid. The record viewer displays the location of a selected fact within the document in response to the fact being selected.

In step 220, the I/O module 120 may detect a change in the facts on the validation viewer GUI. If the change to the fact is validation of an extracted fact, the change is updated to the list of validated facts in step 225. Otherwise, if the I/O module 120 does not detect a change in the facts, the validation module would proceed to step 235.

In step 235, the validation module 110 may determine whether there is a change to the extractions. For example, a user may add a fact by 'swiping' a portion of the text of the document, i.e., highlighting the selected fact. If the validation module 110 determines that there has been a change to the extracted facts, the validation module 110 may determine whether or not a new extraction is needed in step 240.

If the validation module 110 determines that a new extraction is needed, the validation module 110 may be configured to call the extraction module 130 to receive the extracted facts to perform the processing in step 230. Otherwise, the validation module 110 may validate the extracted facts, in step 245.

Returning to step 235, if the validation module 110 determines that there is no change to the extracted facts, the validation module 110 may determine whether or not a change to a current list in step 250.

If the validation module 110 determines a change in the current list, the validation module 110 may be configured to update the current list with the latest change in step 255.

Otherwise, in step 260, the validation module 110 may determine whether or not to save the changes implemented by the user. If the validation module 110 determines that data is to be saved, the validation module 110 may create a revision file in step 265, which is passed onto to a storage device through the storage interface module 140. The revision file may be comprised of the original document, facts made by the software, and changes to the validation status of those facts, changes to the current list, and/or changes made to the temporal status of a fact made during the validation steps described above. The revision file may be used to update later facts. Otherwise, if the validation module 110 determines not to save the changes, the validation module 110 may determine whether or not the user has completed the validation process in step 270. If the user has not completed the validation process, the validation module 110 may return to the processing of step 220. Otherwise, the validation module may invoke the I/O module 120 to close the validation viewer GUI, in step 275.

Figure 3:
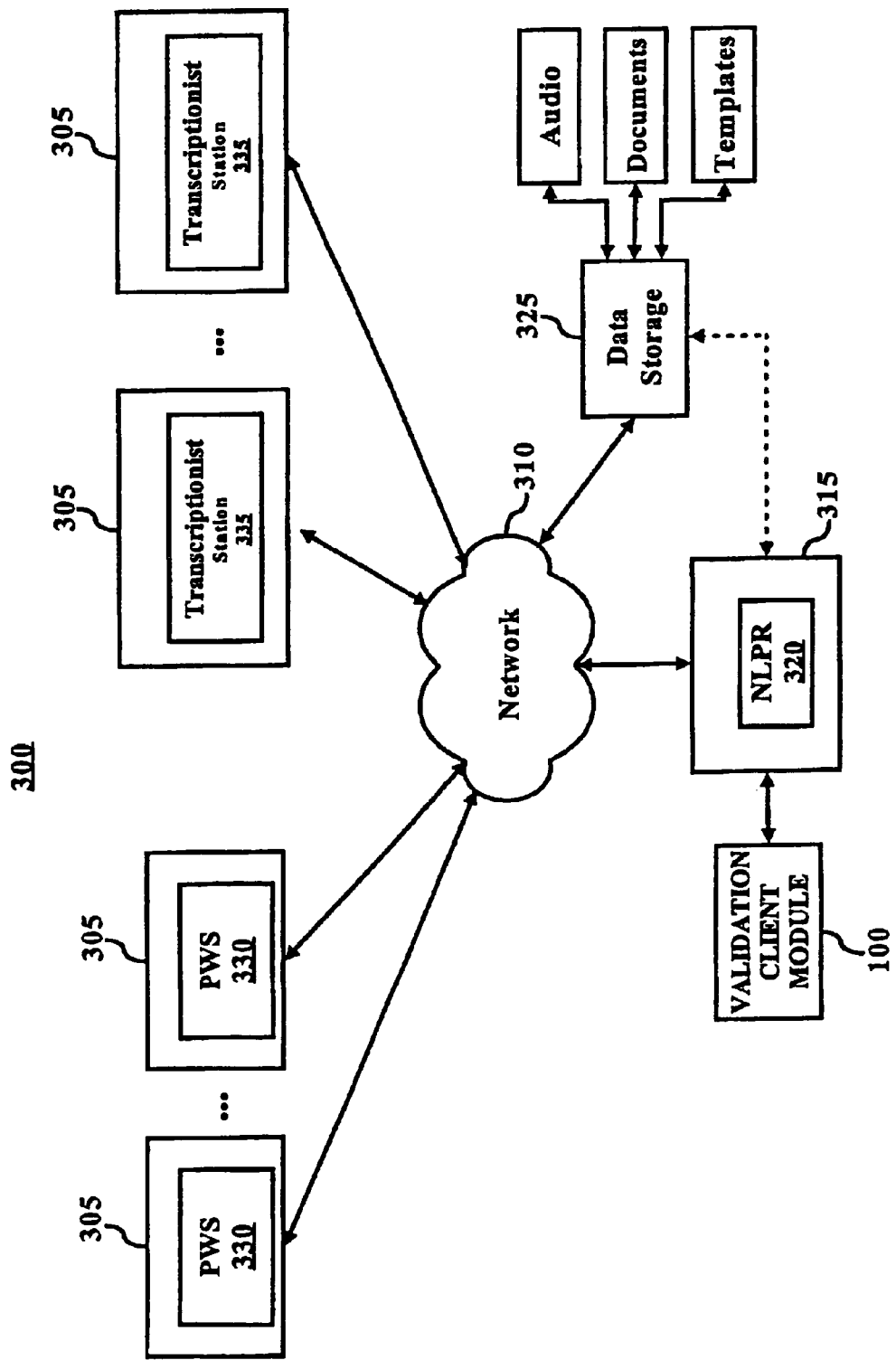
FIG. 3 illustrates a natural language patient record (NLPR) system utilizing the validation client module shown in FIG. 1 in accordance with yet another embodiment of the present invention.

FIG. 3 illustrates a natural language patient record (NLPR) system 300 utilizing a validation client module in accordance with yet another embodiment. As shown in FIG. 3, the NLPR system 300 includes a plurality of workstations 305 interconnected by a network 310. The NLPR system 300 also includes a server 315 executing a computer readable version 320 of the NLPR system and data storage 325. The NLPR system 300 is a system for maintaining electronic medical records of patients, which is described in greater detail in co-pending U.S. patent application Ser. No. 10/447,290, entitled, "SYSTEMS AND METHODS UTILIZING NATURAL LANGUAGE MEDICAL RECORDS," filed May 29, 2003 and published on Dec. 2, 2004 as U.S. Patent Application Publication No. 2004/00243545, which has been incorporated by reference in its entirety.

The workstations 305 may be personal computers, laptops, or other similar computing element. The workstations 305 execute a physician workstation (PWS) client 330 from the NLPR system 300. The PWS client 325 provides the capability for a physician to dictate, review, and/or edit medical records in the NLPR system 300. While FIG. 3 is described in the realm of the medical field, it will be understood by those skilled in the art that the present invention can be applied to other fields of endeavor where users dictate, review and edit records in any domain.

The workstations 305 also execute a transcriptionist client 335 for a transcriptionist to access and convert audio files into electronic text. The NLPR system 300 may also use speech recognition engines to automatically convert dictations from dictators into electronic text.

The network 310 is configured to provide a communication channel between the workstations 305 and the server 315. The network 310 may be a wide area network, local area network or combination thereof. The network 310 may implement wired protocols (e.g., TCP/IP, X.25, IEEE802.3, IEEE802.5, etc.), wireless protocols (e.g., IEEE802.11, CDPD, etc.) or combination thereof.

The server 315 may be a computing device capable of providing services to the workstations 305. The server 315 may be implemented using any commonly known computing platform. The server 315 is configured to execute a computer readable version of the NLPR software 320. The NLPR software provides functionality for the NLPR system 300. The NLPR system 300 may receive audio files and/or documents by other network access means such as electronic mail, file transfer protocols, and other network transferring protocols.

The data storage 325 may be configured to interface with network 310 and provide storage services to the workstations 305 and the server 315. The data storage 325 may also be configured to store a variety of files such as audio, documents, and/or templates. In some embodiments, the data storage 325 includes a file manager (not shown) that provide services to manage and access the files stored therein. The data storage 325 may be implemented as a network-attached storage or through an interface through the server 315.

The server 315 may be further configured to interface with an embodiment of the validation client module 100. A user may invoke the validation client module 100 by through a PWS client 320. For example, the validation client module 100 may be a menu item on a graphical user interface of the PWS client 320. Alternatively, a user may use a command line prompt at the PWS client 320 to invoke the validation client module 100. Once invoked, the validation client module 100 may display a validation viewer GUI as shown in FIG. 4.

FIG. 4 illustrates a validation viewer GUI 400 provided by the validation client module 100 in accordance with yet another embodiment. It should be readily apparent that the elements of the validation viewer GUI 400 may be deleted and/or modified and new elements added.

As shown in FIG. 4, the validation viewer GUI 400 includes a target viewer component 410, a record viewer component 420, and an extraction viewer 430 as generated by the I/O module 120. The target viewer component 410 may be configured to allow editing of validation attributes for each extracted fact (or keyword, concept, term, etc.) through checkboxes and current list icons. Selecting an icon on the target viewer component 410 highlights the associated fact and its corresponding extractions in the extractions viewer 430.

FIG. 5 illustrates the target viewer component 410 in greater detail in accordance with yet another embodiment. It should be readily apparent that the elements of the target viewer component 410 may be deleted and/or modified and new elements added.

As shown in FIG. 5, the target viewer component 410 may include a control bar 502 that includes a 'Finish' button 504, a 'Save' button 506, and an 'Exit' button 508. The Finish button 504 may be configured to save the domain expert's changes to a database, mark the revision of the document as being finished in the database, and close the validation viewer GUI 400, returning the document and its facts to the host application. The Save button 506 may be configured to save the current state of the validation viewer GUI 400 in a database for later completion by the user. The Exit button 508 may be configured to provide the user with the options of exiting the validation viewer GUI 400 without saving or exiting the validation viewer GUI 400 and saving. The options may be presented in a dialog box by the I/O module 120.

When the user is finished validating the facts, the set of facts that have been deleted, added, modified, and validated are sent to the database through the storage interface module 140.

The target viewer component 410 may present the facts in target groups (e.g., as shown in FIG. 5: Problems 510, Medications 512, Allergies 514, Procedures 516, and History 518). Under each target group, the associated facts are displayed. A relevancy checkbox 520 is associated with each fact. If activated, a selected relevancy checkbox 520 may indicate that the associated fact is material to the selected document (or report). The I/O module 120 may also place a status change marker to indicate that the relevancy of the associated fact has changed from a previous report.

The target viewer component 410 also includes a current list icon 524 for each associated fact, as shown in an expanded view in FIG. 5A. The current list icon 524 may be configured to indicate the status of the fact on the current list. By activating the associated current list icon 524 for a selected fact, a user may elect to make the fact Active, Inactive or view the current list.

Returning to FIG. 4, the record viewer component 420 may be configured to display the current document (or record) while the extraction and target viewer components, 430 and 410, respectively, display the extractions and facts for the selected document.

FIG. 6 illustrates a more detailed view of the record viewer component 420 in accordance with yet another embodiment. It should be readily apparent that the elements of the record viewer component 420 may be deleted and/or modified and new elements added.

As shown in FIG. 6, the record viewer component 420 may include mention buttons, previous 602 and next 604. The mention buttons, 602 and 604, may be configured to activate when a selected fact in the target viewer component 410 has multiple mentions in the current report. The context and spans of texts associated with the selected extraction may also be displayed in the extraction viewer 430. Otherwise, if a selected fact has a single mention, the mention buttons, 602 and 604, may be 'ghosted' or deactivated.

When activated, the mention buttons, 602 and 604, may be configured to navigate the report by highlighting the occurrences of the selected fact. Simultaneously, the context for the highlight occurrences will also highlight in the extraction viewer 430.

In the record viewer component 420, a user may add extractions. More particularly, the user may select a whole word(s) within the same sentence. The validation module 110 may be configured not to permit the user to select text in the headings. After selection of text, a user may right-click on the selected text to provide options to send the selected text to as an extraction. For example, the I/O module 120 may display a dialog box that lists the target groups (e.g., Add Problem, Add Medication, Add Procedure, Add Allergy) in the target viewer component.

Returning to FIG. 4, the extraction viewer component 430 may be configured to display the detailed extractions from a highlighted fact in the target viewer component 410. The extraction viewer component 430 may also be configured to simultaneously highlight selected text in the extraction viewer component 430 and the corresponding text in the record viewer component 420.

FIG. 7 illustrates a more detailed view of the extractions viewer component 430 in accordance with yet another embodiment. It should be readily apparent that the elements of the extractions viewer component 430 may be deleted and/or modified and new elements added.

As shown in FIG. 7, the extractions viewer component 430 may display an extraction 702 in one of three states: new, correct or incorrect. A new extraction is one generated by the extraction module 130 that has not yet been validated in any document version. A correct (or validated) extraction has been checked and approved by a user with the appropriate authority to approve the extraction. An incorrect (or deprecated) extraction is one that the user with proper authority has deemed as incorrect.

Associated with each extraction is a status checkbox 704. If a user has placed a check in the checkbox 704, this indicates that the status of the extraction is valid. If a user has placed an 'X' mark in the checkbox 704, this indicates an incorrect or deprecated status for the selected extraction. The checkbox 704 for a new extraction may be defaulted to a state that configured by the user. The extraction viewer component 430 may toggle between a check and 'X' mark in the checkbox 702.

A specific mention can be displayed in context for specific extraction. The span of the text displayed can be any number of characters as desired by the user however it is preferable to display a limited number of characters in width (e.g., 100) so as to limit the context to something easily understood by the user, while achieving and appropriate aspect ratio of leading context to following context based on the characteristics of the language of the text (e.g., 2:1 for English). The actual specific extraction may be distinguished from the surrounding context via font effects. Whole words or partial words may be displayed. When a user selects a particular mention or any part of the mention word string, the line may become highlighted and the corresponding mention may be displayed in the record viewer component 430.

Figure 8:
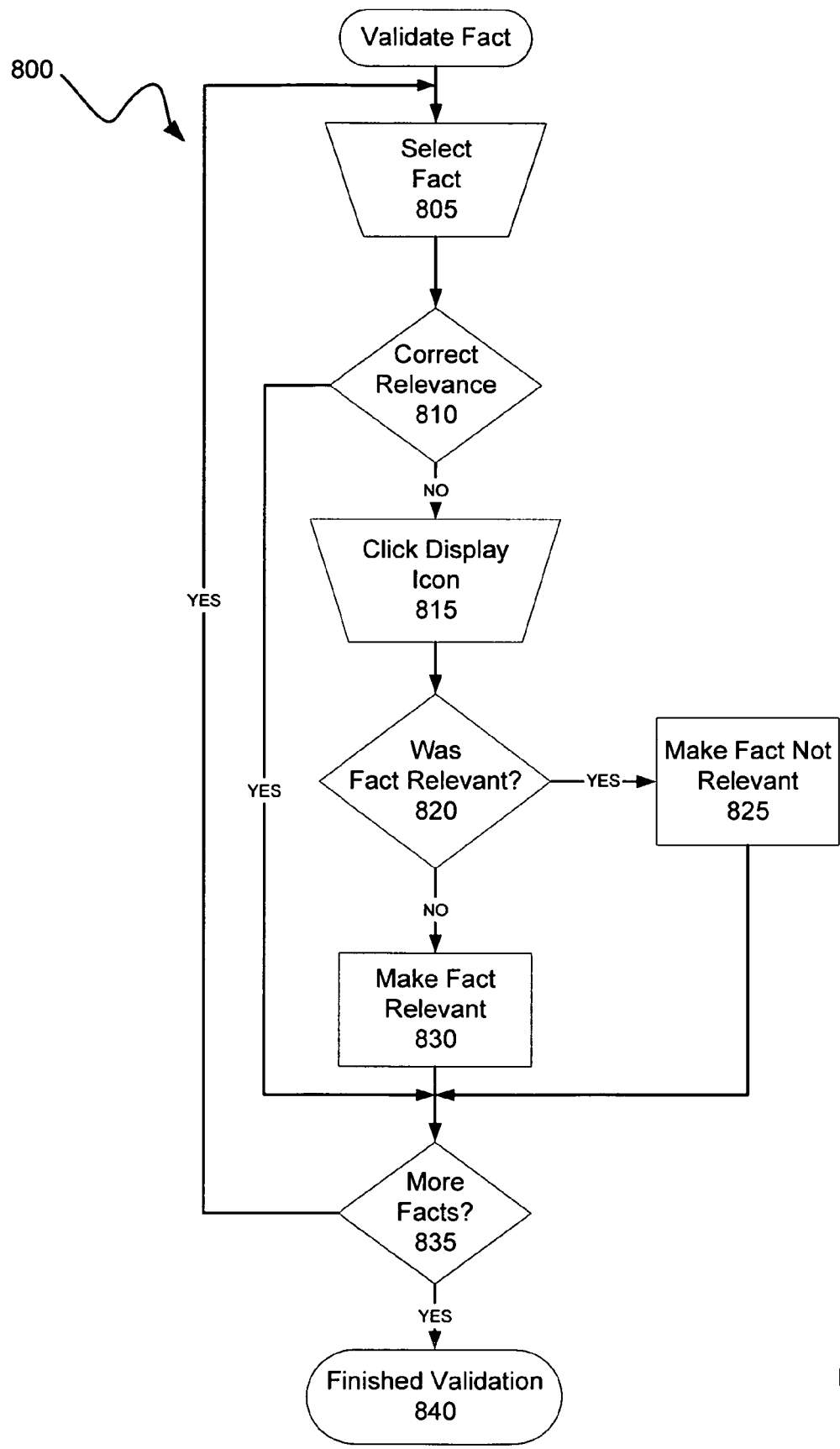
FIG. 8 illustrates a more detailed flow diagram for validating extractions for the validation viewer GUI (shown in FIGS. 4-7) in accordance with yet another embodiment.

FIG. 8 illustrates a more detailed flow diagram 800 for validating facts for the validation viewer GUI 400 (shown in FIGS. 4-7) in accordance with yet another embodiment. It should be readily apparent to those of ordinary skill in the art that this flow diagram 800 represents a generalized illustration and that other steps may be added or existing steps may be removed or modified.

As shown in FIG. 8, a user with proper authority, e.g., a domain expert, may instantiate the process of validating a fact by selecting the fact (e.g., 530 on FIG. 5), in step 805

In step 810, the validation module 110 may determine whether the selected fact has the correct relevance by the action of the user. More specifically, if the user indicates in the relevancy checkbox 520 that the selected fact is not relevant, the user may activate the status marker icon 522 in step 815. Otherwise, the validation module 110 may proceed to the processing of step 835, which is described below.

In step 820, the validation module 110 may determine whether the selected fact was relevant by waiting for a user selection on the status marker icon 522. More particularly, if validation module receives indication from the user that the selected fact is relevant, the user may select the Inactive status to make the fact not relevant, in step 825. Subsequently, the validation module 110 proceeds to the processing of step 835.

Otherwise, if the selected fact was deemed relevant, the user may select the Active status to make the fact relevant, in step 830. Subsequently, the validation module 110 may determine whether the user has selected additional facts for validation, in step 835. If the user selects another fact, the validation module 110 returns to the processing of step 815. Otherwise, the validation module 110 waits for an exit event, in step 840.

Figure 9:
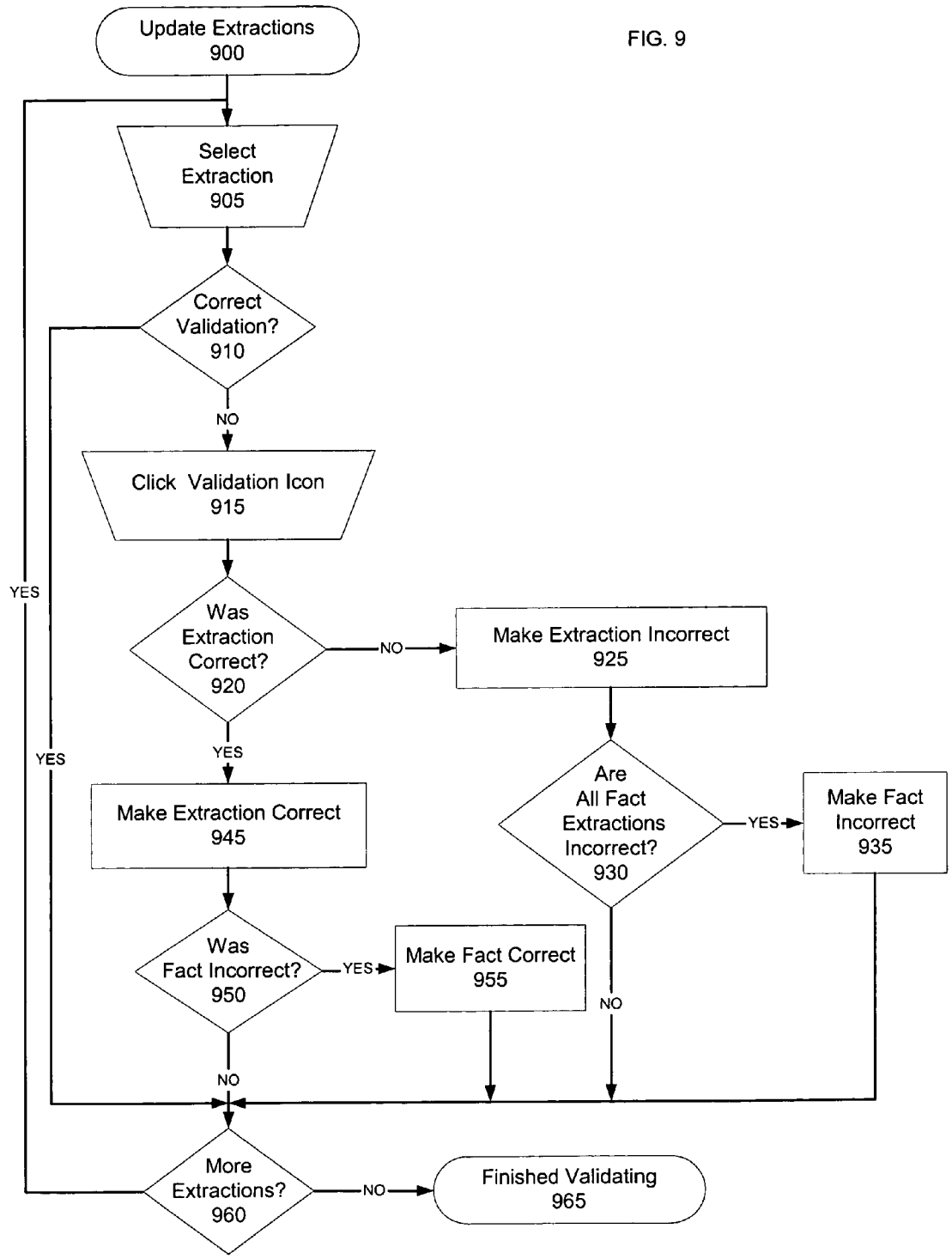
FIG. 9 illustrates a more detailed flow diagram for validating extractions for the validation viewer GUI (shown in FIGS. 4-7) in accordance with yet another embodiment of the present invention.

FIG. 9 illustrates a more detailed flow diagram 900 for validating extractions for the extraction viewer component 430 of the validation viewer GUI 400 (shown in FIGS. 4-7) in accordance with yet another embodiment. It should be readily apparent to those of ordinary skill in the art that this flow diagram 900 represents a generalized illustration and that other steps may be added or existing steps may be removed or modified.

As shown in FIG. 9, a user with proper authority, e.g., a domain expert, may instantiate the process of validating an extraction by selecting the extraction (e.g., 702 on FIG. 7), in step 905

In step 910, the validation module 110 waits for an indication from the user on whether the selected extraction is correct. If the selected extraction is correct, the validation module 110 proceeds to the processing of step 960, as described in greater detail below. Otherwise, if the user indicates that the selected extraction is incorrect, the user may activate (or click) on associated status checkbox 704 (shown in FIG. 7), in step 915. In step 920, the validation module 110 may wait for an indication from the user that the extraction was correct. If the selected extraction was incorrect, the user may change the status of the selected extraction as incorrect by toggling the associated status checkbox 704, in step 925. In step 930, the system may not require additional user feedback. If the system determines that all the extractions have been marked as incorrect, the may automatically mark the associated fact as incorrect in step 935. Alternatively, the validation module 110 may wait for an indication from the user on whether or not all the fact extractions were incorrect. If the all the fact extractions were not incorrect, the validation module 110 may proceed to the processing of step 960. Otherwise, if all the fact extractions are incorrect, the system may mark the associated fact as incorrect by marking the status to Incorrect in check box 704. Subsequently, the validation module may proceed to the processing of step 960.

Returning to step 920, if the user determines that the extraction was correct, the user may toggle the associated status checkbox 704 as correct, in step 945. The validation module 110 then waits for an indication from the user on whether or not the fact was incorrect in step 950. The user may correct the fact in step 955. Subsequently, the validation module 110 proceeds to the processing of step 960.

Otherwise, if the user determines that the fact was correct, the validation module 110 may wait for an indication from the user on whether or not to select additional extractions, in step 960. If there are additional extractions, the validation module 110 returns to the processing of step 905. Otherwise, the validation module 110 waits for an exit event, in step 965.

Figure 10:
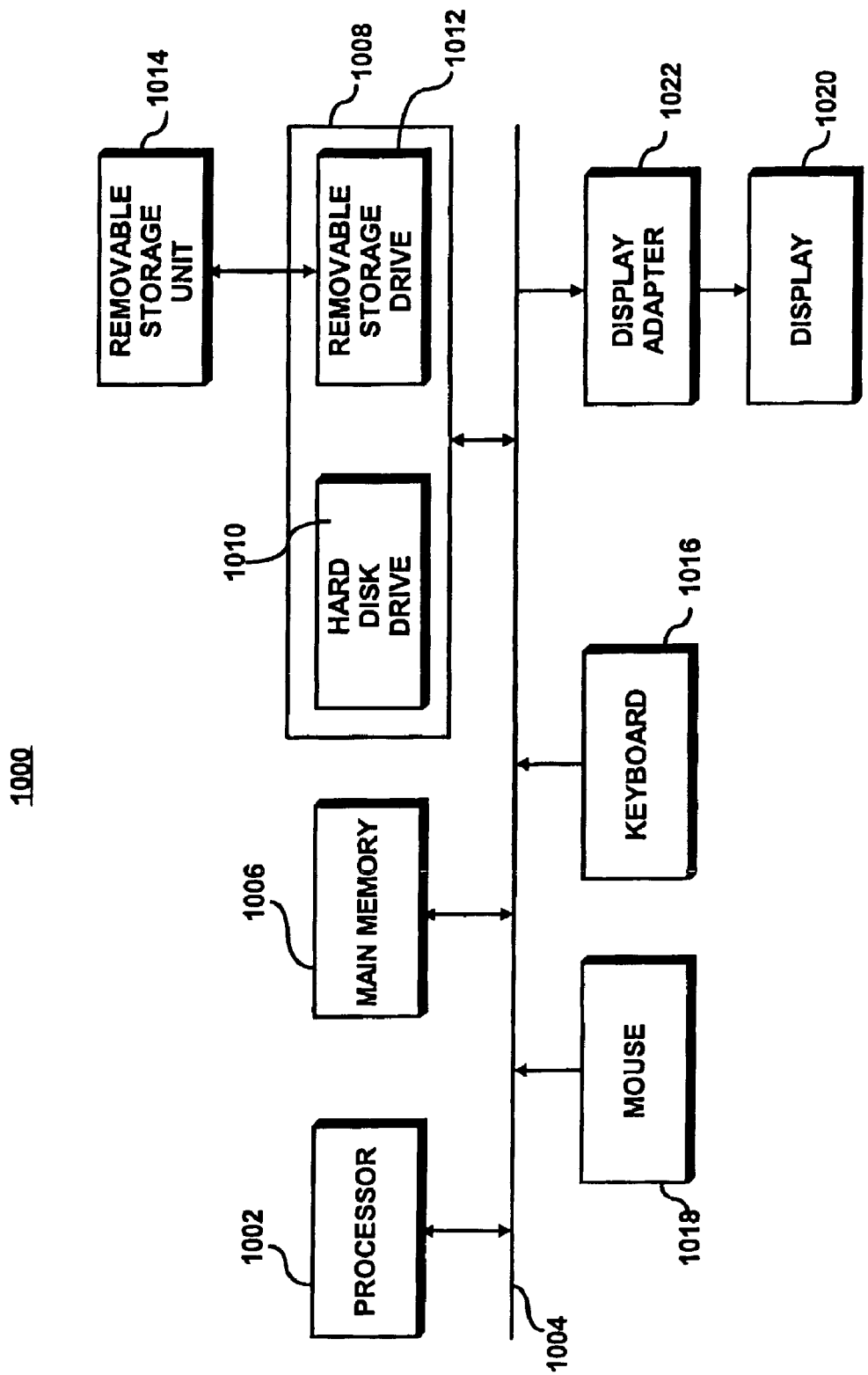
FIG. 10 illustrates an exemplary block diagram of a computer system where an embodiment of the present invention may be practiced.

FIG. 10 illustrates an exemplary block diagram of a computer system 1000 where an embodiment may be practiced. The functions of the validation client module 100 may be implemented in program code and executed by the computer system 1000. The validation client module 100 and the NLPR system 300 may be implemented in computer languages such as PASCAL, C, C++, JAVA, etc.

As shown in FIG. 10, the computer system 1000 includes one or more processors, such as processor 1002, that provide an execution platform for embodiments of the expressway routing module. Commands and data from the processor 1002 are communicated over a communication bus 1004. The computer system 1000 also includes a main memory 1006, such as a Random Access Memory (RAM), where the software for the validation client module 100 may be executed during runtime, and a secondary memory 1008. The secondary memory 1008 includes, for example, a hard disk drive 1010 and/or a removable storage drive 1012, representing a floppy diskette drive, a magnetic tape drive, a compact disk drive, or other removable and recordable media, where a copy of a computer program embodiment for the validation client module may be stored. The removable storage drive 1012 reads from and/or writes to a removable storage unit 1014 in a well-known manner. A user interfaces with the validation client module 100 with a keyboard 1016, a mouse 1018, and a display 1020. The display adaptor 1022 interfaces with the communication bus 1004 and the display 1020 and receives display data from the processor 1002 and converts the display data into display commands for the display 1020.

Certain embodiments may be performed as a computer program. The computer program may exist in a variety of forms both active and inactive. For example, the computer program can exist as software program(s) comprised of program instructions in source code, object code, executable code or other formats; firmware program(s); or other known program. Any of the above can be embodied on a computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes. Exemplary computer readable signals, whether modulated using a carrier or not, are signals that a computer system hosting or running the present invention can be configured to access, including signals arriving from the Internet or other networks. Concrete examples of the foregoing include distribution of executable software program(s) of the computer program on a CD-ROM or via Internet download. In a sense, the Internet itself, as an abstract entity, is a computer readable medium. The same is true of computer networks in general.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method may be performed in a different order than illustrated or simultaneously. Those skilled in the art will recognize that these and other variations are possible within the spirit and scope as defined in the following claims and their equivalents.

What is claimed is:

1. A method for associating documents with searchable metadata, the method comprising:

receiving as input at least one text document; and operating at least one programmed processor to perform acts of creating metadata to be associated with the at least one text document, the metadata comprising at least one text keyword, the creating comprising extracting a set of one or more data elements from text of the at least one text document, the set of one or more data elements comprising at least one keyword that appears in the text of the at least one text document;

normalizing said set of data elements to create a set of normalized data elements, wherein the normalizing comprises, for a first keyword of the at least one keyword, determining at least one other keyword similar to the first keyword, the at least one other keyword not being a keyword appearing in the text of the at least one text document, and adding the at least one other keyword to the set of normalized data elements;

identifying at least one previously-validated keyword that is associated as metadata with at least one previously-stored text document, the at least one previously-stored text document not being one of the at least one text document, the at least one previously-validated keyword not being in the set of normalized data elements;

merging said set of normalized data elements with the at least one previously-validated keyword to form a preliminary set of data elements;

presenting said preliminary set of data elements for review by a user; and receiving user input validating a validated set of data elements; and in response to the user input validating the validated set of data elements, storing the at least one text document and storing the validated set of data elements as the metadata, the metadata being associated with the at least one text document such that the at least one text document may be located through a search for any data element included in the validated set of data elements.

2. The method according to claim 1, wherein extracting a set of data elements from the text comprises extracting at least one data element from the text that is an element from the group consisting of facts described in the text and concepts described in the text.

3. The method according to claim 1, wherein receiving said at least one text document comprises receiving a plurality of documents related by a common characteristic.

4. The method according to claim 3, wherein receiving the plurality of documents related by the common characteristic comprises receiving the plurality of documents related by a characteristic from a group consisting of chronology, subject, and indexing key.

5. The method according to claim 1, wherein normalizing a data element of the set of data elements comprises normalizing the data element based on a SNOMED standard, and wherein determining at least one other data element comprises determining a SNOMED code.

6. The method according to claim 1, wherein normalizing a data element of the set of data elements comprises normalizing the data element based on a ICD-9-CM standard, and wherein determining at least one other data element comprises determining a ICD-9-CM code.

7. The method according to claim 1, wherein normalizing a data element of the set of data elements comprises normalizing the data element based on a CPT standard, and wherein determining at least one other data element comprises determining a CPT code.

8. The method according to claim 1, wherein extracting the set of one or more data elements comprises extracting a set of one or more data elements relating to a medical subject matter or to a patient or to a medical subject matter and a patient.

9. The method according to claim 8, wherein extracting the set of one or more data elements relating to a medical subject matter comprises extracting at least one data elements relating to medical subject matter from the group consisting of allergies, medications, diagnoses, ailments, and physicians.

10. The method according to claim 1, wherein presenting the preliminary set of data elements for review comprises displaying the preliminary set of data elements on a graphical display.

11. The method according to claim 10, further comprising operating the at least one processor to perform:
during the displaying of the preliminary set of data elements on the graphical display, when a preliminary data element of the set of preliminary data elements is selected, displaying a portion of said at least one document relating to the preliminary data element on the graphical display.

12. The method according to claim 1, wherein the creating further comprises:
identifying the at least one keyword by examining a set of one or more previously-stored documents to identify documents related to the at least one text document.

13. The method according to claim 12, wherein examining to identify documents related to the at least one text document comprises identifying the documents based on a K-nearest neighbor algorithm.

14. The method according to claim 12, wherein examining to identify documents related to the at least one text document comprises identifying the documents based on a cosine similarity metric.

15. The method according to claim 11, wherein displaying the portion of said at least one document relating to the preliminary data element comprises displaying the portion of the document from which a data element related to the preliminary data element was extracted.

16. The method according to claim 15, wherein displaying the portion of said at least one document relating to the preliminary data element comprises displaying the portion of the document from which the preliminary data element was extracted.

17. The method according to claim 1, wherein the creating further comprises:
receiving, in response to the presenting, at least one change to the preliminary set of data elements;
changing the preliminary set of data elements based on the at least one change; and
in response to the user input, identifying the changed preliminary set of data elements as the validated set of data elements.

18. The method according to claim 1, wherein the creating further comprises:
in response to the user input, identifying the preliminary set of data elements as the validated set of data elements.

19. The method according to claim 1, wherein the creating further comprises:
retrieving, for a preliminary data element of the preliminary set of data elements, at least one change previously made to a similar preliminary data element when the similar preliminary data element was associated with at least one other document; and
changing the preliminary data element according to the at least one change prior to presenting the preliminary set of data elements.

20. The method according to claim 1, wherein normalizing said set of data elements further comprises adding the first data element to the set of normalized data elements.

21. A computer-usable medium having computer-readable instructions stored thereon for execution by a processor, wherein the instructions, when executed by the processor, cause the processor to perform a method for associating documents with searchable metadata, the method comprising:
receiving as input at least one text document;
creating metadata to be associated with the at least one text document, the metadata comprising at least one text keyword, the creating comprising:
extracting a set of one or more data elements from text of the at least one text document, the set of one or more data elements comprising at least one keyword that appears in the text of the at least one text document;
normalizing said set of data elements to create a set of normalized data elements, wherein the normalizing comprises, for a first keyword of the at least one keyword, determining at least one other keyword similar to the first keyword, the at least one other keyword not appearing in the text of the at least one document, and adding the at least one other keyword to the set of normalized data elements;
identifying at least one previously-stored document by examining a set of one or more previously-stored documents to identify documents related to the at least one text document;
merging said set of normalized data elements with at least one previously-validated keyword that is associated as metadata with the at least one previously-stored document to form a preliminary set of data elements, the at least one previously-validated not being in the set of normalized data elements;
presenting said preliminary set of data elements for review by a user; and receiving user input validating a validated set of data elements; and in response to the user input validating the validated set of data elements, storing the at least one text document and storing the validated set of data elements as the metadata, the metadata being associated with the at least one text document such that the at least one text document may be located through a search for any data element included in the validated set of data elements.

22. The computer-usable medium of claim 21, wherein the creating further comprises:

receiving, in response to the presenting, at least one change to the preliminary set of data elements;

changing the preliminary set of data elements based on the at least one change; and in response to the user input, identifying the changed preliminary set of data elements as the validated set of data elements.

23. The computer-usable medium of claim 21, wherein the creating further comprises:

in response to the user input, identifying the preliminary set of data elements as the validated set of data elements.

24. The computer-usable medium of claim 21, wherein the creating further comprises:

retrieving, for a preliminary data element of the preliminary set of data elements, at least one change previously made to a similar preliminary data element when the similar preliminary data element was associated with at least one other document; and changing the preliminary data element according to the at least one change prior to presenting the preliminary set of data elements.

25. The computer-usable medium of claim 21, wherein normalizing said set of data elements further comprises adding the first data element to the set of normalized data elements.

26. An apparatus for associating documents with searchable metadata, the apparatus comprising:

at least one processor programmed to:

receive as input a text document;

create metadata to be associated with the at least one text document, the metadata comprising at least one text keyword, the at least one processor being programmed to create at least in part by:

extracting a set of one or more data elements from text of the text document, the set of one or more data elements comprising at least one keyword that appears in the text of the text document;

normalizing said set of data elements to create a set of normalized data elements, wherein the normalizing comprises, for a first keyword of the at least one keyword, determining at least one other keyword similar to the first keyword, the at least one other keyword not appearing in the text of the text document, and adding the at least one other keyword to the set of normalized data elements;

identifying at least one previously-validated keyword that is associated as metadata with at least one previously-stored text document, the at least one previously-validated keyword not being in the set of normalized data elements;

merging said set of normalized data elements with the at least one previously-validated keyword to form a preliminary set of data elements for the text document;

presenting said preliminary set of data elements for review by a user; and following presenting said preliminary set of data elements to the user and in response to user input validating a validated set of data elements store the text document and store the validated set of data elements as metadata associated with the text document such that the at least one text document may be located through a search for any data element included in the validated set of data elements.

27. The apparatus of claim 26, wherein the at least one processor is further programmed to create by:

identify the at least one previously-stored document by examining a set of one or more previously-stored documents to identify documents related to the at least one text document.

28. The apparatus of claim 26, wherein the at least one processor is further programmed to create by:

receive, in response to the presenting, at least one change to the preliminary set of data elements;

change the preliminary set of data elements based on the at least one change; and in response to the user input, identify the changed preliminary set of data elements as the validated set of data elements.

29. The apparatus of claim 26, wherein the at least one processor is further programmed to create by:

in response to the user input, identifying the preliminary set of data elements as the validated set of data elements.

30. The apparatus of claim 26, wherein the at least one processor is further programmed to create by:

retrieve, for a preliminary data element of the preliminary set of data elements, at least one change previously made to a similar preliminary data element when the similar preliminary data element was associated with at least one other document; and change the preliminary data element according to the at least one change prior to presenting the preliminary set of data elements.

31. The apparatus of claim 26, wherein the at least one processor is further programmed to normalize said set of data elements by adding the first data element to the set of normalized data elements.

* * * * *